United States Patent [19]
Kato et al.

[11] Patent Number: 4,512,871
[45] Date of Patent: Apr. 23, 1985

[54] OXYGEN SENSOR WITH HEATER

[75] Inventors: Nobuhide Kato, Aichi; Takao Murase, Konan, both of Japan

[73] Assignee: NGK Insulators, Ltd., Japan

[21] Appl. No.: 604,473

[22] Filed: Apr. 27, 1984

[30] Foreign Application Priority Data

May 9, 1983 [JP] Japan .............................. 58-68663[U]
May 9, 1983 [JP] Japan .............................. 58-68664[U]
Dec. 23, 1983 [JP] Japan ............................ 58-202830[U]
Dec. 23, 1983 [JP] Japan ............................ 58-202831[U]

[51] Int. Cl.³ ..................................... G01N 27/58
[52] U.S. Cl. .................................... 204/429; 204/427; 204/428
[58] Field of Search ............... 204/427, 428, 429, 1 S; 60/276; 123/489; 204/424

[56] References Cited

U.S. PATENT DOCUMENTS 4,175,019 11/1979 Murphy .............................. 204/429
4,212,720 7/1980 Maurer et al. ..................... 204/424
4,437,971 3/1984 Csanitz et al. ..................... 204/427

Primary Examiner—G. L. Kaplan
Attorney, Agent, or Firm—Parkhurst & Oliff

[57] ABSTRACT

An oxygen sensor having a bar-shaped heater inserted in an elongate bore formed in a tubular solid electrolyte body which has porous platinum electrodes on its inner and outer surfaces and which is supported by a housing such that its closed end portion is exposed to exhaust gas and such that the elongate bore is gas-tight with respect to the exhaust gas. The bar-shaped heater comprises a heating resistor having a positive temperature coefficient, a ceramic body carrying the heating resistor so as to embed the latter, and a pair of lead wires. The ceramic body has on its periphery a pair of terminal pads connected to the heating resistor. The ends of the lead wires are brazed to the pads with a mass of brazing material containing silver. An exposed surface of the brazing mass is coated with a metal layer made of metal which is different from silver or its alloy. The metal layer may be further coated with a heat-resistant layer.

15 Claims, 7 Drawing Figures

OXYGEN SENSOR WITH HEATER

BACKGROUND OF THE INVENTION

The present invention relates generally to an oxygen sensor for detecting concentration of oxygen contained in exhaust gas emitted from an internal combustion engine. More particularly, the invention is concerned with such an oxygen sensor having a bar-shaped heater disposed in an elongate bore formed in a tubular solid electrolyte body.

In the art of controlling an air-fuel (A/F) ratio of an internal combustion engine for an automotive vehicle or for other applications, it is known to use an oxygen sensor which employs a mass of zirconia or other solid oxygen-ion conductive electrolyte to detect a content or concentration of oxygen in exhaust gas produced by the engine, according to the principle of an oxygen concentration cell. For example, such an oxygen sensor uses a solid electrolyte body of zirconia which is provided on its inner and outer surfaces with porous platinum electrodes, respectively. The electrode on the inner surfaces which defines an inner elongate bore in the zirconia body, is exposed to an ambient atmosphere and serves as a reference electrode (anode) which is exposed to a reference gas whose oxygen concentration is known. On the other hand, the electrode provided on the outer surface of the zirconia body is exposed to exhaust gas to be measured, so that this electrode serves as a measuring electrode (cathode) to monitor oxygen content of the exhaust gas. This oxygen sensor measures the oxygen concentration in the exhaust gas by measuring an electromotive force which is induced in response to a difference in the oxygen concentration between the reference and measuring electrodes.

However, the induced electromotive force is unstable until the solid electrolyte has been heated to a given point. This, the above type of oxygen sensor suffers a drawback that is incapable of effecting an accurate control of an air-fuel ratio of the engine while the temperature of the exhaust gas of the engine is relatively low, for example while the engine is idling or immediately after the engine is started in its cold condition.

To solve such a drawback experienced in the art, it has been proposed to positively heat a solid electrolyte body by inserting a heater into an elongate cylindrical hole formed in the electrolyte body. For instance, Japanese Patent application laid open in 1979 under Publication No. 54-13396 discloses a heater which consists of an insulator bar and a heating wire (resistance wire) wound on the surface of the insulator bar. Further, Japanese Patent application laid open in the same year under Publication No. 54-22894 shows a so-called sheathed heater which uses a resistance coil wire disposed in a metal sleeve which is filled with a powdered electrically insulating material of high thermal conductivity so as to secure the coil wire in the metal sleeve.

Such proposed oxygen sensors equipped with a heater are disadvantageous in that their solid electrolyte is susceptible to excessive heat when the temperature of the exhaust gas of an internal combustion engine is elevated, whereby the porous platinum electrodes tend to be sintered with a result of reducing a rate of reaction of the measuring electrode to the exhaust gas, or a spinel coating layer protecting the electrodes tends to crack or flake off. Further, the heater is subject to an excessively high temperature due to a combined effect of its self-heating and exposure to heat of the exhaust gas, thereby suffering breakage of its inner resistance wire.

On the other hand, an effort to restrain heat generation of the heater to minimize such disadvantages as indicated above, will create another incovenience of insufficient heating of the solid electrolyte while the exhaust gas is low in temperature, or undesired requirement of extra time for heating the solid electrolyte after the start of the engine, before the electromotive force induced by the sensor reaches a level for accurate detection of the oxygen concentration.

The above inconvenience of insufficient heating of the solid electrolyte is serious, particularly when a battery voltage to actuate the heater is low, that is, immediately after the engine is started or while the engine is operated in a cold state. On the contrary, when the battery voltage rises with the engine speed, the temperature of the exhaust gas is elevated. This will aggravate the previously indicated drawback of excessive heating of the solid electrolyte.

Further, a heater used in the traditional oxygen sensor suffers a problem of migration of silver which is used as a brazing material for connecting lead wires to electric terminals of the heater. More particularly, the silver ions migrate or move from one of the electric terminals to the other, under the influence of electric field during a long period of power application to the heater. This migration phenomenon of silver causes short-circuiting of the electric terminals.

SUMMARY OF THE INVENTION

It is accordingly an object of the present invention to provide an oxygen sensor having an improved heater inserted in an elongate bore formed in a body of solid electrolyte, which is durable and reliable in operation even in comparatively varying environmental conditions, and which is substantially free from a problem of migration of a brazing material used to connect lead wires to the heater.

According to the present invention, there is provided an oxygen sensor comprising: a tubular solid electrolyte body having an elongate bore which is closed at one end of the tubular body and open at the other end, and further having reference and measuring electrodes on inner and outer surfaces thereof, respectively; a housing which supports or retains the body of solid electrolyte such that the outer surface of the latter is exposed at the closed end to exhaust gas, and such that the elongate bore in the tubular solid electrolyte body is held in gas-tight condition with respect to the exhaust gas; and a bar-shaped heater inserted in the elongate bore in the tubular solid electrolyte body. The bar-shaped heater comprises a heating resistor having a positive temperature coefficient, a ceramic body carrying the heating resistor so as to embed the heating resistor, and a pair of lead wires for connecting the heating resistor to an electric power source. The ceramic body has, on its outer peripheral surface a pair of terminal pads connected to the heating resistor. An end portion of each of the lead wires is brazed to corresponding one of the terminal pads with a mass of brazing material containing silver as one of its components. An exposed surface of the mass of brazing material is coated with a metallic layer made of metal which is different from silver or its alloy.

In the oxygen sensor constructed as described above wherein the heating resistor supported and protected by the ceramic body has a positive temperature coefficient, the heater provides a relatively large amount of heat when the temperature of the exhaust gas is comparatively low, but provides a relatively small amount of heat when the exhaust gas temperature is comparatively high, whereby the solid electrolyte is heated to a sufficient level within a short length of time after the start of elevation of the exhaust gas, and the solid electrolyte and the heating resistor are less likely to be overheated even when the sensor is exposed to the exhaust gas of high temperature. Further, the brazing material applied to connect the lead wires to the terminal pads connected to the heating resistor, is coated with a metallic material to cover the exposed surface of the mass of the applied brazing material. Since the metallic coating material is selected from a group of metals, except silver, which do not undergo migration under the influence of electric field, the silver contained in the brazing material is prevented by the metallic coating layer from migrating from one of the terminal pads towards the other. Thus, the metallic coating layer serves to avoid otherwise possible short-circuiting of the electric terminals of the bar-shaped heater. With the above arrangements, the oxygen sensor according to the invention is capable of providing reliable electrical outputs accurately representing oxygen concentration of an exhaust gas from an internal combustion engine, and therefore capable of controlling an air-fuel ratio of the engine with high precision and for a prolonged period of service.

According to one preferred aspect of the invention, the mass of brazing material coated with the metallic layer may be further coated with a heat-resistant layer, preferably made of an inorganic material.

In accordance with an advantageous form of the invention, the metallic layer is provided in the form of a metal plating, preferably an electroless or chemical plating. Further, nickel is used as an advantageous material for the metallic layer.

According to a further advantageous aspect of the invention, the positive temperature coefficient of the heating resistor is not less than 0.3%/°C., so that the principle of the invention is practiced more effectively.

BRIEF DESCRIPTION OF THE DRAWING

The above and other objects, features and advantages of the present invention will be better understood from reading the following description of the preferred embodiments taken in connection with the accompanying drawing in which.

DETAILED DESCRIPTION OF THE PREFERRED EMBODIMENTS

Figure 2:
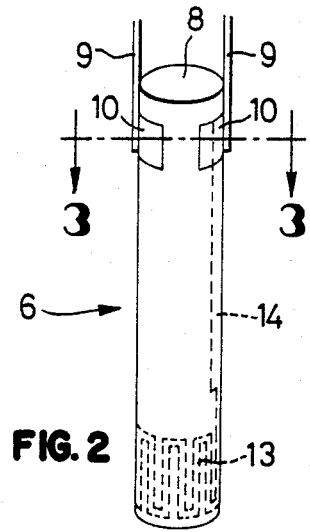
FIG. 2 is a schematic perspective illustration of one form of the bar-shaped heater used in the oxygen sensor of FIG. 1(a)
Figure 3:
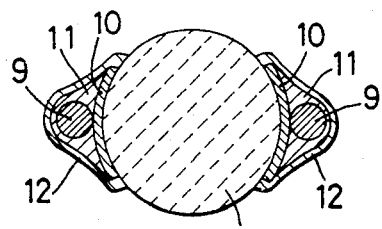
FIG. 3 is a cross sectional view taken along line 3—3 of FIG. 2.
Figure 4:
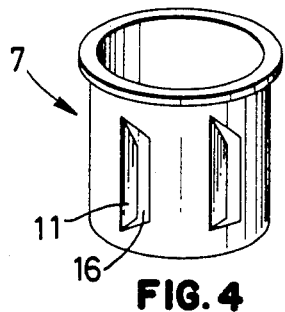
FIG. 4 is a perspective view of one form of a protective metal tube used in the oxygen sensor of FIG. 1(a)

Referring first to FIGS. 1-4, there is illustrated a preferred form of an oxygen sensor embodying the present invention, wherein a tubular solid electrolyte body 1 such as zirconia is supported by a housing 2. The tubular body 1 has an elongate cylindrical bore 1a which is formed longitudinally of the body 1. The elongate bore 1a is closed at one end of the body 1 which is exposed to exhaust gas emitted through an exhaust conduit (not shown), for example, from an internal combustion engine of an automotive vehicle. The elongate bore 1a is open, at the other end of the tubular body, to ambient atmosphere used as a reference gas. The tubular solid electrolyte body 1 is provided at its inner and outer surfaces with a reference electrode 1b (anode) and a measuring electrode 1c (cathode), respectively, as shown in FIG. 1(b), both electrodes 1b and 1c being made of porous platinum. The tubular body 1 is retained and sealed in the housing 2, via a talc 3, a metal washer 4 and a metal ring 5, such that the elongate bore 1a is held in gas-tight condition with respect to the exhaust gas, i.e., so that the ambient atmosphere (air) and the exhaust gas do not meet with each other. In the elongate bore 1a, there is inserted a bar-shaped heater 6 to heat the tubular solid electrolyte body 1. The closed end portion of the tubular body 1 is enclosed by a protective metal tube 7, which protects the closed end portion against direct exposure thereof to a stream of the exhaust gas flowing through the exhaust conduit. The protective metal tube 7 is fixed at its upper end to the lower end of the housing 2, and has flute openings 16 in its peripheral wall to introduce the exhaust gas into the interior of the tube 7 for exposure of the lower or closed end portion of the electrolyte body 1 to the exhaust gas. These flute openings 16 are formed by cutting parts of the peripheral wall and bending these cut parts radially inwardly of the protective metal tube 7 so as to form louver plates 11, as illustrated in FIG. 4.

Figure 1A:
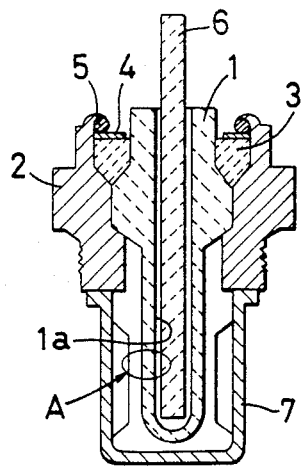
FIG. 1(a) is an elevational view in cross section of one embodiment of an oxygen sensor with a heater of the present invention.
Figure 1B:
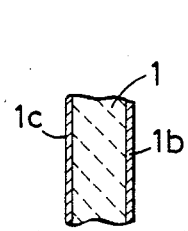
FIG. 1(b) is an enlarged fragmentary view in cross section of a portion A of a tubular solid electrolyte body of the oxygen sensor of FIG. 1(a)

The bar-shaped heater 6 inserted in the elongate bore 1a of the tubular solid electrolyte body 1 as shown in FIG. 1(a), comprises a ceramic body 8 made of ceramics such as alumina, as shown in FIGS. 2 and 3. The ceramic body 8 carries a heating resistor in the form of a printed heating portion 13 (FIG. 2), such that the heating resistor is embedded in the mass of the ceramic body 8. The heating portion 13 is connected to a pair of printed lead portions 14 which are connected to a corresponding pair of terminal pads 10. The heating portion 13 and the lead portions 14 are respectively imprints of electrically resistant and conductive materials which are applied in a paste state to the surface of a ceramic bar to form a predetermined printed pattern, as shown in broken lines in FIG. 2. The ceramic bar with the heating and lead portions 13 and 14 is covered with a ceramic layer to constitute the ceramic body 8. The ends of the lead portions 14 not connected to the heating portion 13 penetrate the ceramic layer to reach the outer peripheral surface of the ceramic body 8, so that the lead portions 14 are connected to the terminal pads 10. The lead portions 14 are connected to an electric power source through a corresponding pair of lead wires 9. Each lead wire 9 is brazed at its one end to corresponding one of the pair of terminal pads 10. As illustrated in a cross sectional view of FIG. 3 taken along line 3—3 of FIG. 2, the pair of terminal pads 10 are provided on the outer peripheral surface of the bar-shaped ceramic body 8. More specifically, the pads 10 are disposed along parts of the peripheral surface of the ceramic body 8, such that they are electrically connected to the lead portions 14 and consequently to the heating portion 13. The end portions of the lead wires 9 and the corresponding terminal pads 10 are brazed together by applying a suitable brazing material 11 containing silver. The mass of applied brazing material 11 surrounds the periphery of the respective lead wire 9. An exposed surface of the mass 11 is coated with a metallic layer 12. The material of this metallic layer 12 is selected from metals except silver. In other words, the metallic coating layer 12 is made of metal which is different from silver or its alloy. For example, the metallic layer 12 is formed of nickel. This metallic coating layer 12 may be provided in a suitable manner, for example, by applying a plating of a suitable metal, preferably by using a chemical plating process.

The heating portion 13 used as the heating resistor in the bar-shaped ceramic heater 6 has a positive temperature coefficient of 0.5%/°C. With this selection of the positive temperature coefficient, the resistance of the heating resistor (heating portion 13) is increased and its amount of heat generation is decreased as the temperature of the exhaust gas is elevated, whereby otherwise possible overheating of the solid electrolyte 1 and the heater 6 is prevented at the elevated temperature of the exhaust gas. On the other hand, when the exhaust gas temperature is relatively low, the resistance of the heating resistor 13 is held low and its amount of heat generation is increased, thereby making it possible to raise the temperature of the solid electrolyte 1 to a level at which an accurate electromotive force is induced by the electrodes 1b, 1c, in a comparatively short time after the start of the vehicle engine in its cold state, or making it possible to heat the solid electrolyte 1 sufficiently while the engine is idling.

Figure 5:
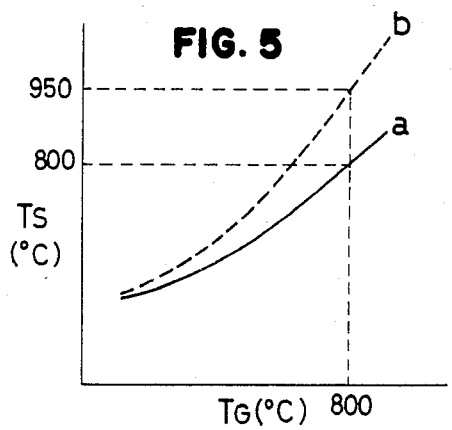
FIG. 5 is a graphical representation of a solid electrolyte temperature in relation to an exhaust gas temperature in the oxygen sensor of the invention, as compared with that in an oxygen sensor known in the art.

A graph of FIG. 5 shows a temperature $T_S$ (°C.) of the solid electrolyte 1 in relation to a temperature $T_G$ (°C.) of the exhaust gas, wherein a curve (a) represents the relation between the temperatures $T_S$ and $T_G$ obtained on the ceramic heater of the instant oxygen sensor, and a curve (b) represents the same relation obtained on a known sheathed heater employing a nichrome wire which is selected so that a length of time from the start of a cold engine to generation of an electromotive force from a sensor using the sheathed heater is substantially equal to that of the oxygen sensor of the invention. At the exhaust temperature of 800° C., the temperature of the solid electrolyte 1 heated by the ceramic heater 6 of the invention is 800° C. as shown by the curve (a), while the temperature of a solid electrolyte heated by the known sheathed heater is 950° C. as indicated by the curve (b). This graph indicates less heating of the electrolyte by the ceramic heater 6 and consequently reduced chance of overheating of the electrolyte when the exhaust temperature $T_G$ is relatively high.

Experiments were conducted, on the oxygen sensor of the invention and the known oxygen sensor used in the measurements of FIG. 5, to check for outlook or appearance of the solid electrolytes and physical condition of the heaters after these sensors are placed in continuous service for 300 hours at an exhaust gas temperature of 800° C. The results on the known sensor showed some cracks of a spinel coating layer which is applied to the outer surface of the solid electrolyte body, and 70% breakage of resistance wire of the sheathed heater. On the oxygen sensor of the invention, neither such cracks nor such breakage were found.

As indicated above, the ceramic heater 6 using the printed heating portion 13 having a positive temperature coefficient, has a relatively low level of resistance of the heating element at low exhaust temperatures, and consequently an increased amount of heat generation from the heater, thereby allowing a rapid heating of the solid electrolyte and consequently an earlier generation of an electromotive force from the sensor. This advantage is obtained, for example, immediately after the start of a cold engine, or when the engine is running at its idling speed. On the contrary, a rise of the exhaust temperature to a considerably higher level will cause an appreciable increase in the resistance of the heating portion 13. For example, the resistance at 800° C. is approximately five times as high as that at the room temperature. Thus, the possibility of overheating of the solid electrolyte body 1 and the heater 6 is minimized. It is noted that a positive temperature coefficient of the heating portion 13 is important to the heat regulating or controlling performance of the heater 6 as discussed above. In the case where the oxygen sensor is used for an internal combustion engine, it is preferred that the positive temperature coefficient of the heating resistor 13 be held not less than 0.3%/°C. This coefficient which should be a positive value, is determined by kinds of electrically resistant metal powders selected for the heating resistor 13, and by an amount of glass frits contained in the paste of such metal powders.

In a common oxygen sensor, an Ag-Cu-Zn eutectic hard solder or a brazing material containing Ag as one of its components is widely used to connect lead wires to electric terminals of a bar-shaped heater. It is recognized in the art that the Ag content of the solder or brazing material migrates between the electric terminals, and the migration may cause short-circuiting of the terminals or cracking at these electrical connections on the heater. This migration of silver is a phenomenon wherein Ag ions produced through ionization of AgOH or $Ag_2O$ will drift or move, under the influence of electric field, towards one or the other electric terminal.

In the light of the above phenomenon, the instant ceramic heater 6 employs the metallic coating layer containing no Ag, preferably an electroless plating layer, in order to cover an exposed surface of the mass of brazing material 11 which is applied to braze the lead wires 9 to the terminal pads 10. Thus, the metallic layer prevents the ionization of Ag and consequently prevents the Ag content of the brazing material from migrating between the two terminals. The metallic layer further serves to prevent reaction of the Ag component of the brazing material with a gas with which silver easily reacts, for example, prevents the reaction of the Ag component with a sulfide gas and resulting formation of silver sulfide.

As indicated previously, the metallic layer 12 may be formed in various known methods such as plating, and the metal material for this layer may be selected from metals except Ag, which do not undergo the above discussed migration, i.e., selected from metals which are different from silver or its alloy. For example, the metallic layer 12 may be formed of nickel (Ni), zinc (Zn), gold (Au) or the like. Nickel is particularly excellent in heat and corrosion resistances. It is generally preferred that the metallic layer 12 be provided as a nickel plating layer, in particular as a plating layer of a nickel-phosphorus (Ni-P) alloy containing about 10% of phosphorus, which is recommended from the standpoint of preventing the formation of pin holes and obtaining highly dense adhesion to the brazing material 11. Further, it is preferable to form the metallic layer 12 with a thickness of not less than one micron.

While the ceramic heater 6 of the present embodiment uses the printed heating portion 13 embedded in the ceramic body 8, the heating resistor used according to the invention may be provided in the form of an embedded resistance wire made of tungsten, nickel, platinum or the like, or on other forms as long as the heating resistor is formed of a material which has a positive temperature coefficient. As for the position of the heating resistor in the ceramic body 8, it is desired that the heating resistor be located within a portion of the tubular solid electrolyte body 1 which is exposed to an exhaust gas to be monitored by the sensor.

Figure 6:
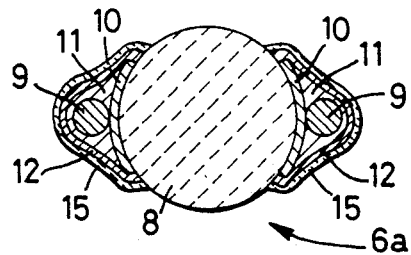
FIG. 6 is a cross sectional view, corresponding to FIG. 3, showing another form of the bar-shaped heater used according to the invention.

Referring next to FIG. 6, there is illustrated another preferred embodiment of the oxygen sensor of the invention. The same reference characters as used in FIGS. 2 and 3 will be used in these figures to identify corresponding components.

This embodiment uses a bar-shaped heater 6a which is different from the heater 6 of FIGS. 1–3, in that the entire surface of the metallic layer 12 of the heater 6a is coaed with a heat-resistant layer 15 formed of a suitable heat-resistant material. As in the preceding embodiment, the metallic layer 12 of the heater 6a may preferably be formed by a suitable plating method, in particular an electroless or chemical plating method. This embodiment of the oxygen sensor having the ceramic heater 6a with the heat-resistant layer 15 showed a result similar to that indicated by the curve (a) of FIG. 5 in association with the first embodiment. Further, the additional formation of the heat-resistant layer 15 covering the metallic layer 12 assures more effective prevention of the previously described migration phonomenon of the Ag component of the brazing material 11.

The heat-resistant layer 15 may be formed of any known heat-resisting materials such as, silicone, fluorinated resin, inorganic materials, etc. However, the use of inorganic materials is preferable because of their excellent heat resistance. Further, it is appreciated that the water absorption of the heat-resistant layer 15 be held not greater than 1% (percentage of weight increase after 72 hours of exposure to 95% relative humidity at room temperature), in order to maximize the capability of preventing the previously indicated reaction of silver and its migration.

While the present invention has been described in its preferred embodiments, it is to be understood that the invention is not limited thereto but may be otherwise embodied within the scope of the appended claims.

What is claimed is:

1. An oxygen sensor comprising:
   a tubular solid electrolyte body having an elongate bore which is closed at one end of said tubular solid electrolyte body and open at the other end, and further having reference and measuring electrodes on inner and outer surfaces thereof, respectively;
   a housing supporting said tubular solid electrolyte body such that said outer surface thereof is exposed at said one end to exhaust gas, said housing maintaining said elongate bore in gas-tight condition with respect to said exhaust gas; and
   a bar-shaped heater inserted in said elongate bore in said tubular solid electrolyte body, and comprising a heating resistor having a positive temperature coefficient, a ceramic body carrying said heating resistor so as to embed the heating resistor, and a pair of lead wires for connecting said heating resistor to an electric power source,
   said ceramic body having on its outer peripheral surface a pair of terminal pads connected to said heating resistor, an end portion of each of said lead wires being brazed to corresponding one of said terminal pads with a mass of brazing material containing silver, an exposed surface of said mass of brazing material being coated with a metallic layer made of metal which is different from silver or its alloy.

2. An oxygen sensor as recited in claim 1, wherein said metallic layer is a metal plating.

3. An oxygen sensor as recited in claim 2, wherein said metal plating is an electroless plating.

4. An oxygen sensor as recited in claim 3, wherein said electroless plating comprises nickel.

5. An oxygen sensor as recited in claim 2, wherein said metal plating comprises nickel.

6. An oxygen sensor as recited in claim 1, wherein said positive temperature coefficient is not less than 0.3%/°C.

7. An oxygen sensor as recited in claim 1, wherein said metallic layer has a thickness of not less than one micron.

8. An oxygen sensor comprising:
   a tubular solid electrolyte body having an elongate bore which is closed at one end of said tubular solid electrolyte body and open at the other end, and further having reference and measuring electrodes on inner and outer surfaces thereof, respectively;
   a housing supporting said tubular solid electrolyte body such that said outer surface thereof is exposed at said one end to exhaust gas, said housing maintaining said elongate bore in gas-tight condition with respect to said exhaust gas; and
   a bar-shaped heater inserted in said elongate bore in said tubular solid electrolyte body, and comprising a heating resistor having a positive temperature coefficient, a ceramic body carrying said heating resistor so as to embed the heating resistor, and a pair of lead wires for connecting said heating resistor to an electric power source,
   said ceramic body having on its outer peripheral surface a pair of terminal pads connected to said heating resistor, an end portion of each of said lead wires being brazed to corresponding one of said terminal pads with a mass of brazing material containing silver, an exposed surface of said mass of brazing material being coated with a metallic layer made of metal which is different from silver or its alloy, said metallic layer being coated with a heat-resistant layer.

9. An oxygen sensor as recited in claim 8, wherein said heat-resistant layer is made of an inorganic material.

10. An oxygen sensor as recited in claim 8, wherein said metallic layer is a metal plating.

11. An oxygen sensor as recited in claim 10, wherein said metal plating is an electroless plating.

12. An oxygen sensor as recited in claim 11, wherein said electroless plating comprises nickel.

13. An oxygen sensor as recited in claim 10, wherein said metal plating comprises nickel.

14. An oxygen sensor as recited in claim 8, wherein said positive temperature coefficient is not less than 0.3%/°C.

15. An oxygen sensor as recited in claim 8, wherein said metallic layer has a thickness of not less than one micron.

* * * * *